United States Patent [19]

Powell

[11] Patent Number: 5,749,859
[45] Date of Patent: May 12, 1998

[54] CATHETER OR CANNULA SYSTEM

[75] Inventor: Andrew Robert Powell, Largs Bay, Australia

[73] Assignee: Parashar Holdings Pty Ltd, Adelaide, Australia

[21] Appl. No.: 656,232

[22] PCT Filed: Dec. 9, 1994

[86] PCT No.: PCT/AU93/00763

§ 371 Date: Aug. 27, 1996

§ 102(e) Date: Aug. 27, 1996

[87] PCT Pub. No.: WO95/15779

PCT Pub. Date: Jun. 15, 1995

[30] Foreign Application Priority Data

Dec. 10, 1993 [AU] Australia .................. PM2895

[51] Int. Cl.⁶ ........................ A61M 5/178; A61M 5/00
[52] U.S. Cl. ................... 604/167; 604/169; 604/250; 604/256
[58] Field of Search ....................... 604/164, 165, 604/167, 169, 247, 249, 250, 264

[56] References Cited

U.S. PATENT DOCUMENTS

| | | | |
|---|---|---|---|
| 3,794,223 | 2/1974 | Patel | 604/249 X |
| 4,243,034 | 1/1981 | Brandt | 604/169 |
| 4,936,542 | 6/1990 | Beard. | |
| 4,960,259 | 10/1990 | Sunnanvader et al. | 604/250 X |
| 5,312,373 | 5/1994 | Freitas | 604/249 |
| 5,429,616 | 7/1995 | Schaffer | 604/250 |
| 5,458,581 | 10/1995 | Hull | 604/250 X |
| 5,542,933 | 8/1996 | Marks | 604/167 X |

FOREIGN PATENT DOCUMENTS

| | | |
|---|---|---|
| 0 150 666 | 8/1985 | European Pat. Off. . |
| 1064445 | 5/1954 | France . |
| 2 052 364 | 4/1972 | Germany . |
| 2 206 076 | 10/1972 | Germany . |
| 30 39 591 | 5/1982 | Germany . |
| 39 34 776 | 9/1990 | Germany . |
| 2 075 347 | 11/1981 | United Kingdom . |

*Primary Examiner*—Sam Rimell
*Assistant Examiner*—Robert V. Racunas
*Attorney, Agent, or Firm*—Evenson, McKeown, Edwards & Lenahan, P.L.L.C.

[57] ABSTRACT

A catheter or cannula (2) which includes a press or pinch point (18) which may be resiliently deformed to prevent flow of blood or other body fluids during insertion of the catheter or cannula tube (10) or it may be part of the boss (11) of the catheter or cannula (2). One or more protrusions or buttons (20) may be integrally moulded to the press or pinch point (18) to assist with the application of pressure to the press or pinch point (18) to prevent fluid flow. Wings (14) extending from the sides of the cannula or catheter (2) may provide support and be hinged to enable compression of the press or pinch point (18). The cathether or cannula tube (10) is of a size to fit over a hypodermic needle (5) of a trocar (1) inserted into the catheter or cannula (2).

29 Claims, 7 Drawing Sheets

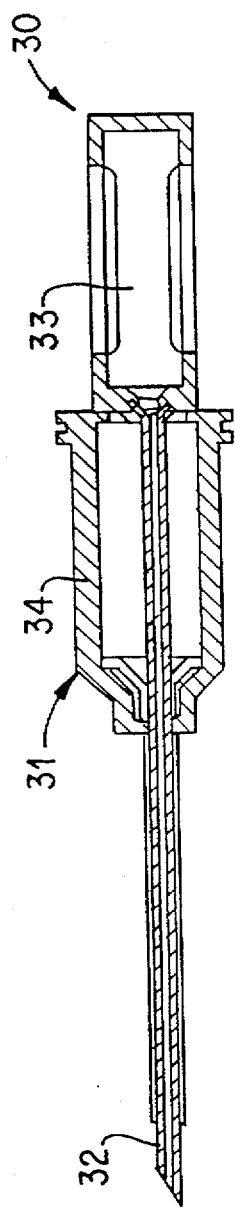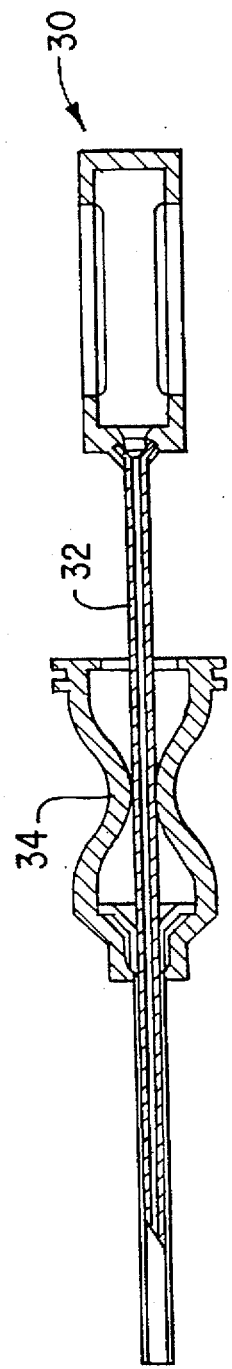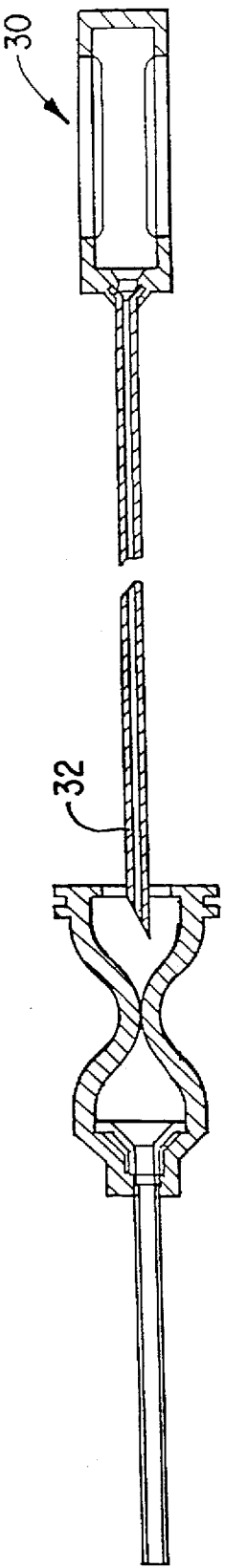

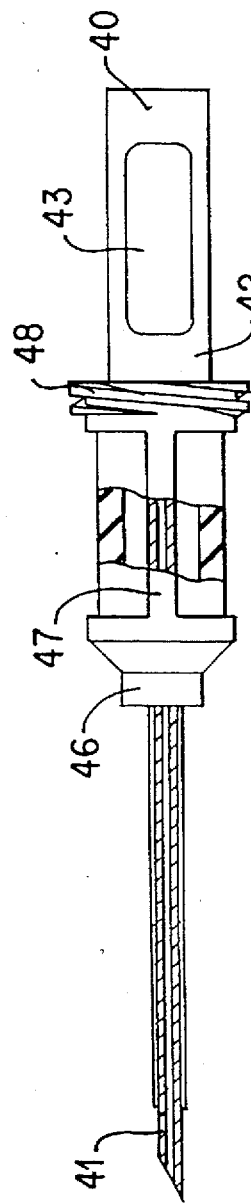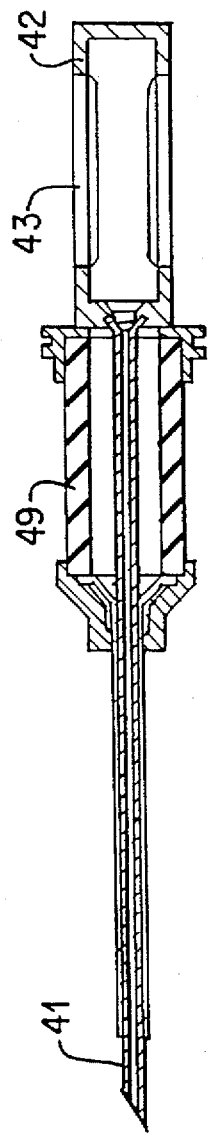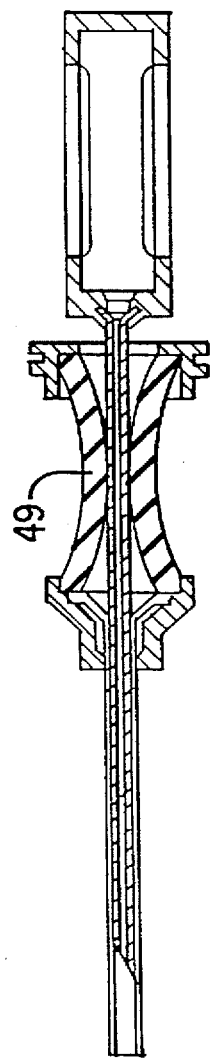

CATHETER OR CANNULA SYSTEM

TECHNICAL FIELD

This invention relates to an improvement to systems which use an artificial tube for supply to or extraction of fluids from a human or animal body.

BACKGROUND ART

The insertion of a tube into a human or animal in many cases requires a hole to be pierced through the skin. For this purpose a device known as a trocar, a catheter or a cannula may be used. A trocar is a sharp pointed instrument adapted to punch the wall of the body. The trocar may have a catheter or cannula mounted onto it and upon removal of it from the catheter or cannula fluid may be extracted. A catheter is a tubular flexible instrument passed into a body cavity or channel for withdrawal of fluids from or introduction of fluids into the body cavity or channel. A cannula is for inserting into a duct or cavity in a body. During its insertion its lumen may be occupied by a stylet or trocar. A stylet is a wire adapted to run through a catheter or cannula to render it stiff or to remove debris from its lumen.

One specialized form of trocar or stylet is a hypodermic needle having a splash back with a window so that during insertion when blood is seen in the window it is known that a vein or artery has been pierced.

Generally in this specification and claims the word cannula will be used to describe either a catheter or cannula and trocar will be used to define a trocar, stylet or splash back.

Generally a catheter or cannula with a stylet or trocar or combination of these is used as an artificially inserted tube into a human or animal body either for the delivery of fluids into the body or the removal of fluids from the body. In one method a catheter or cannula assembly is inserted into a vein of an animal or human and the trocar or stylet is removed to leave the cannula or catheter in place. At the time of removal of the catheter or cannula there can be a problem with loss of blood and perhaps of more concern a danger with infection by blood or body fluid borne diseases. In the past there has been no reasonable solution to prevent this loss of blood.

It is the object of this invention to provide an arrangement by which the loss of blood or other body fluids is able to be restricted during the process of insertion of an artificial tube such as a catheter or cannula assembly into a human or animal body.

DISCLOSURE OF THE INVENTION

In one form the invention is said to reside in a catheter or cannula of the type to be mounted on to a trocar, the catheter or cannula incorporating a press or pinch point which is adapted to be resiliently deformed by externally applied pressure by at least one finger of a person during the insertion of the catheter or cannula tube and trocar assembly into a patient and removal of the trocar so as to prevent a flow of fluid through the catheter or cannula during the insertion and removal, wherein the catheter or cannula is of a type including a boss and a catheter or cannula tube and the portion which is adapted to be resiliently deformed is part of the boss.

The press point may be associated with the catheter or cannula assembly or may be as an attachment which can be fastened onto a catheter or cannula assembly.

It will be seen that generally by this invention, that the press point can be used during the insertion of the catheter or cannula assembly and during removal of a trocar or stylet used to make the catheter or cannula rigid during insertion to stop blood flow until a suitable connection has been made to the catheter or cannula for whatever purpose. When in the non-pinched state the pinch point of course does not provide any restriction to the insertion of the hypodermic needle of the stylet, trocar or splash back.

In an alternative form the invention may be said to reside in a catheter or cannula including a boss and a catheter or cannula tube, the boss including a first portion into which the catheter or cannula tube is mounted and a connection portion which enables the catheter or cannula to be connected to another item, characterised by a press or pinch point associated with the boss between the first portion and the connector portion, the press or pinch point being adapted to be pinched by externally applied pressure to restrict flow through the catheter or cannula during the insertion of the catheter or cannula into a patient, wherein the first portion and the connector portion are connected by a frame arrangement and the press or pinch point is included on a flexible rubber or plastics material tube received into the frame arrangement between the first portion and the connector portion and sealingly engaging the first portion and the connector portions respectively.

The catheter or cannula may generally be of a type including a boss, a tube and a connecting portion. The at least one portion which is adapted to be resiliently deformed may be at the base of the tube adjacent the boss, or alternatively the portion may be included as part of the boss or may be between the boss and the connecting portion.

This resiliently deformable portion of the catheter or cannula may be made from a flexible or elastomeric or plastics material such as silicone rubber.

Alternatively the portion of the catheter or cannula which is adapted to be resiliently deformed can be an adaptor piece which can be fitted to an existing catheter or cannula by the use of known types of medical connectors for provision of a pinch point onto such an item.

In an alternative form the invention may be said to reside in an adaptor piece for a catheter or cannula, the adaptor piece comprising a first end portion onto which the catheter or cannula may be mounted and a connection end portion to enable the adaptor piece to be connected to another item, characterised by a press or pinch point being between the first end portion and the connector end portion, wherein the first end portion and the connector end portion are connected by a frame arrangement and the press or pinch point is included on a flexible rubber or plastics material tube received into the frame arrangement between the first end portion and the connector end portion and sealingly engaging the first end portion and the connector end portion respectively.

The pinch point may be a soft flexible plastics material or rubber portion.

The entire boss may be made of a soft flexible rubber or plastics material and be adapted to be resiliently deformed to provide the pinch point.

Alternatively the first portion and the connector portion may be connected by a frame assembly with the pinch portion being a soft flexible rubber or plastics material tube received into the frame assembly between the first portion and the connector portion and sealingly engaging the first portion and the connector portions respectively. The pinch portion may comprise merely a tube portion or a tube with one or two projections or buttons extending from it to enable more positive compression of the tube and so as to ensure that the fingers of a user are well away from the point of the stylet, trocar or splash back.

In an alternative embodiment the pinch portion may include a more positive action arrangement obtained from valve pieces which can be squeezed together to more positively close off the flow path. Such valve pieces may be spring loaded and biased towards a valve open position so that upon release of the pinch portion, the tube will open again for transfer of fluids into or out of the body. When in the open position the stylet or trocar or hypodermic needle may be inserted between the valve pieces.

The catheter or cannula arrangement of the present invention may include wings extending from the sides of the catheter or cannula to bear against the body of a person or animal into which the catheter or cannula is being inserted to provide a stable operating surface for the activation of the press point. In one embodiment the wings may be hinged on hinge axes aligned with the length of the catheter or cannula and may be hinged to bear against the pinch point and resiliently deform the press point.

The artificial tube, catheter or cannula according to this invention may be used to enable closing off of blood flow during insertion of an intravenous cannula. Such an intravenous catheter or cannula may be used for an intravenous drip, anaesthetic supply, saline drip, addition of blood expanders or pharmaceuticals or may be used for such things as urinary catheters, wound drains, naso-gastric tubes or naso-oral-gastric tubes or any other tube through which fluids may flow.

It may be particularly noted that the present application may have veterinary applications as well as applications with the human body.

This then generally describes the invention but to assist with understanding the invention reference will now be made to the accompanying drawings which show preferred embodiments of the invention.

BRIEF DESCRIPTION OF THE DRAWINGS

In the drawings

FIGS. 4A to 4C shows a cross-sectional view of an alternative embodiment of a catheter or cannula assembly according to this invention in various stage of operation, FIGS. 5A to 5F shows a cross-sectional view of an alternative embodiment of a catheter or cannula assembly according to this invention in various stage of operation.

BEST MODE FOR CARRYING OUT THE INVENTION

Figure 1:
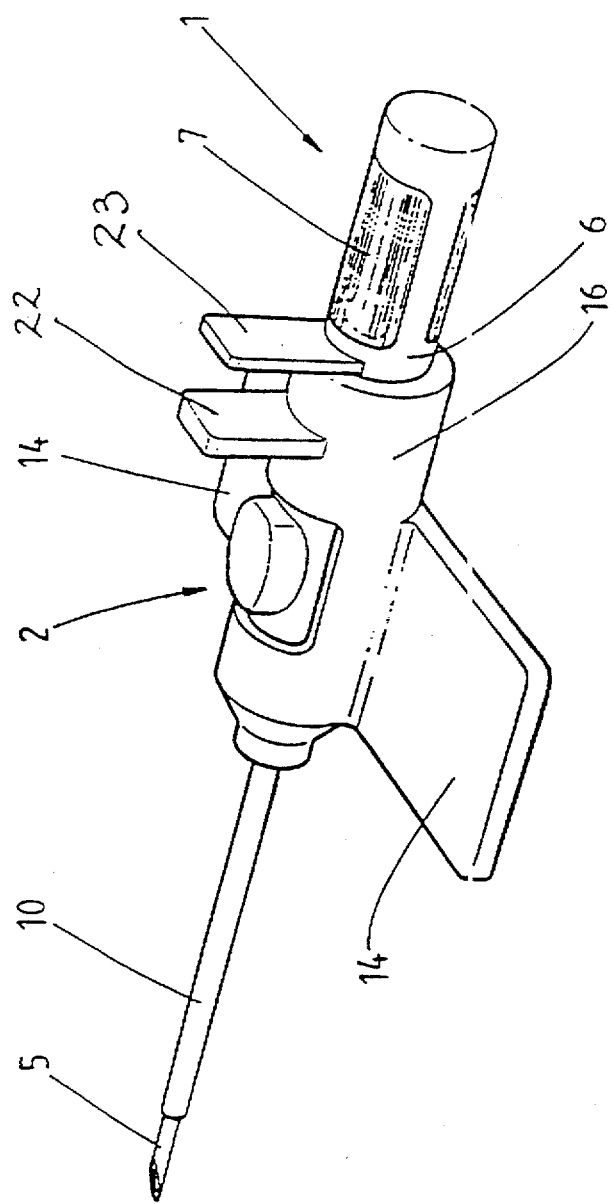
FIG. 1 shows a perspective view of a first embodiment of a catheter or cannula assembly of the present invention.
Figure 2:
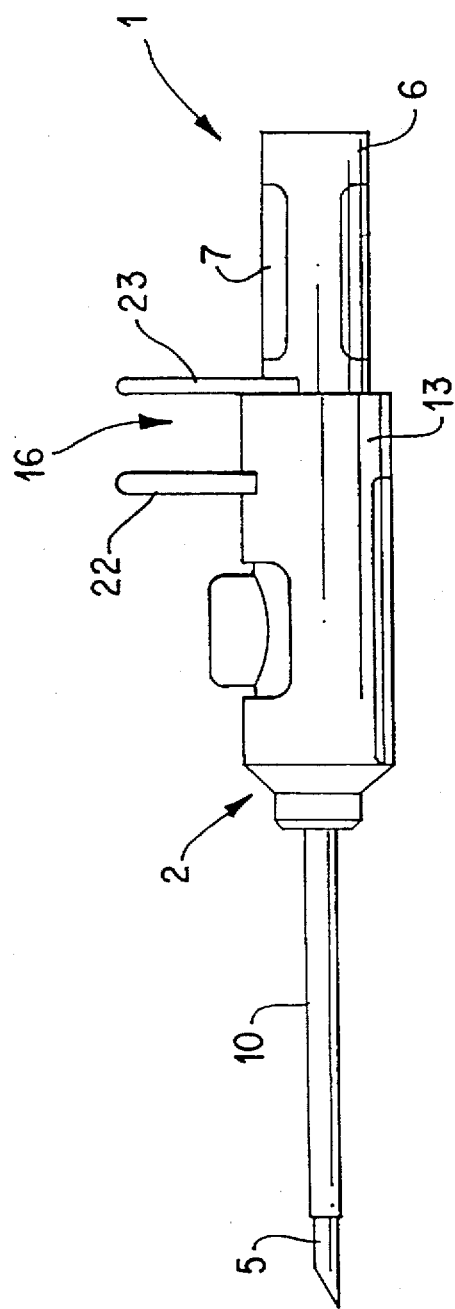
FIG. 2 shows a side view of the embodiment shown in FIG. 1.
Figure 3:
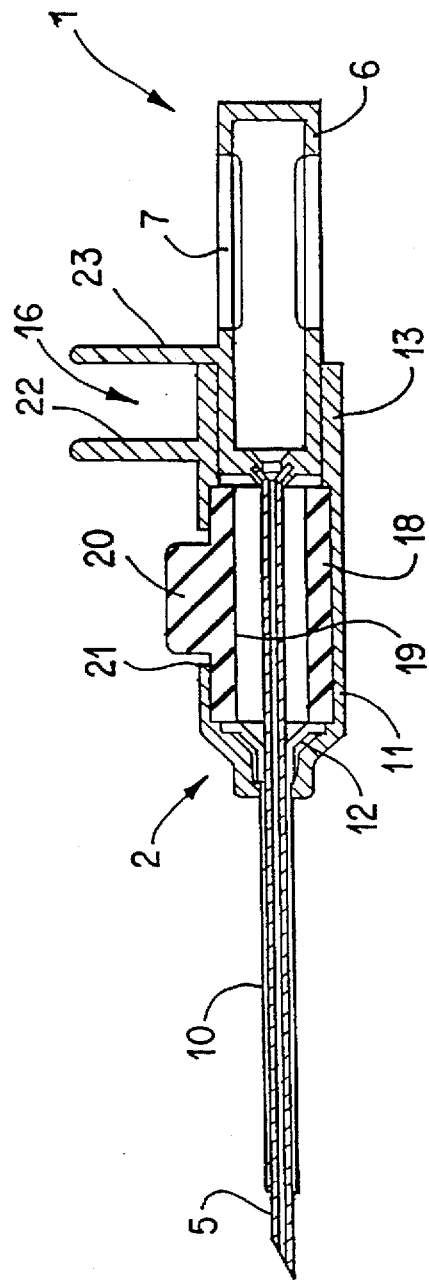
FIG. 3 shows a cross sectional view of the embodiment of FIG. 1.

Now looking more closely at the drawings and in particular the embodiment shown in FIGS. 1 to 3 the cannula assembly of this embodiment comprises a trocar generally shown as 1 inserted into a cannula generally shown as 2. The trocar comprises a hypodermic needle 5 mounted into a base 6. The base 6 includes a translucent or transparent window portion 7.

The cannula includes a cannula tube 10 generally of a plastics material and of a size to just fit over the hypodermic needle 5 of the trocar 1. The cannula tube 10 is fitted into a boss 11 on the cannula body 13 by means of a conical stainless steel clamping ring 12. The body 13 of the cannula includes wings 14 extending out to each side of the body. The body 13 terminates in a connecting portion 16 into which some item of medical equipment such as an intravenous drip tube connector may be inserted. The body includes within it a resilient tube 18 with an aperture 19 therethrough large enough for insertion therethrough of the hypodermic needle 5. The tube portion 18 includes a button 20 integrally moulded into it extending through an aperture 21 in the body 13. When the hypodermic needle 5 of the trocar 1 is not inserted into the cannula 2 then pressure on the button 20 can close off the flow path through the cannula defined by the tube 18.

In use therefore with the cannula and trocar assembly joined together the hypodermic needle is inserted into the body of a patient and during insertion observation of the window portion 7 is made so that when blood is seen it will be realised that a vein has been located. During insertion the cannula and trocar are held together by the finger grips 22 and 23. The cannula is then held in place by means of fingers on the wings 14 and finger grip 23 thumb grip 22 while withdrawing the trocar from the assembly and maintaining pressure on the button 20 until the needle 5 has been removed and the pressure on the button 20 closes off the flow path through the cannula. A suitable item of medical equipment such as an intravenous drip tube connector is then connected to the connecting portion 16. Adhesive tape may be taped over the wings 14 onto the body of the patient to hold the cannula in place.

The embodiment shown in FIGS. 4A to 4C comprises a catheter 31 and a trocar 30. The trocar includes a hypodermic needle 32 mounted into the base 33 of the trocar 30. The boss 34 of the cannula is comprised of flexible plastics material so that as shown in FIG. 4B as the needle 32 is removed the boss 34 can be squeezed with the fingers of one hand until shown in FIG. 4C the needle 32 is completely removed and the flow path through the cannula is closed off.

In the embodiment shown in FIGS. 5A to 5F the trocar 40 includes a hypodermic needle 41 mounted into a base 42 which includes a window 43.

Figure 5D:
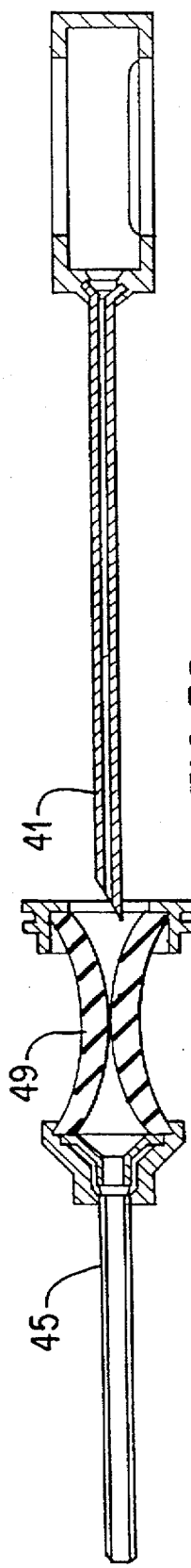
Figure 5E:
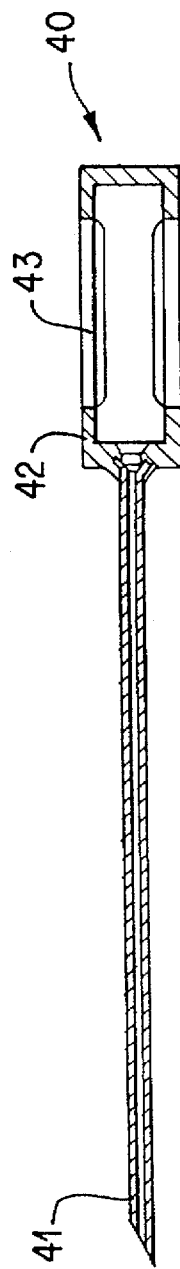
Figure 5F:
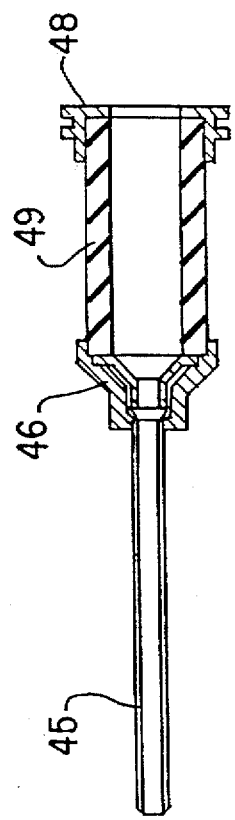

The cannula part as particularly seen in FIG. 5F comprises a cannula tube 45 mounted into a boss 46 the boss 46 has a strap member 47 extending to a connecting portion 48 with a flexible elastomeric tube 49 extending between the boss and the connecting portion and sealably engaging to each of these.

As can particularly be seen in FIGS. 5C and 5D as the hypodermic needle 41 is withdrawn from the cannula the flexible plastics tube 49 can be compressed until it completely closes off the flow path through the cannula until a suitable item of medical equipment has been connected.

Figure 6A:
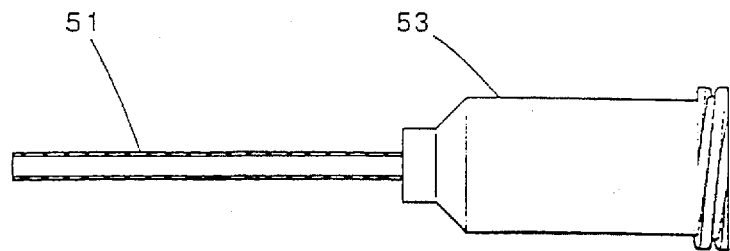
FIGS. 6A and 6B show a side view of an alternative embodiment of a catheter or cannula assembly according to this invention.
Figure 6B:
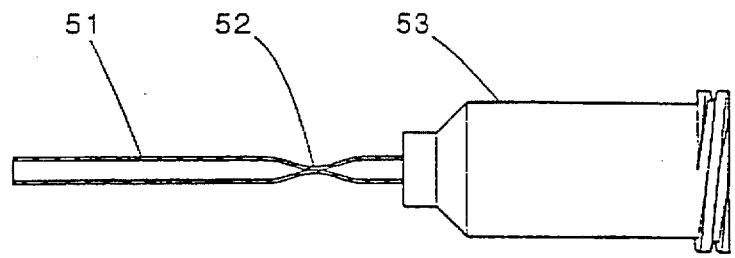

FIG. 6A and 6B show two views of an alternative embodiment of cannula according to this invention. In this embodiment the portion of the cannula which can be squeezed to close off the flow path includes part of the cannula tube 51 which can be compressed at the portion 52 where it mounts into the boss 53. In this embodiment the boss 53 can be made from a rigid plastics material.

Figure 7:
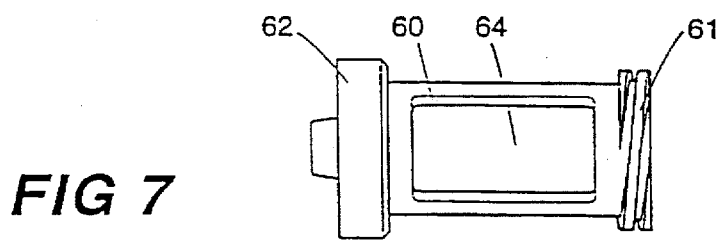
FIG. 7 shows an alternative embodiment of a pinch point arrangement of the present invention in this case being on an attachment for a catheter or cannula assembly.
Figure 8:
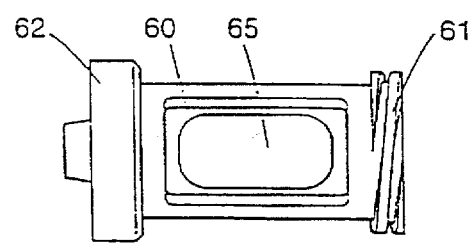
FIG. 8 shows a further embodiment of press point on an attachment of the present invention.
Figure 9:
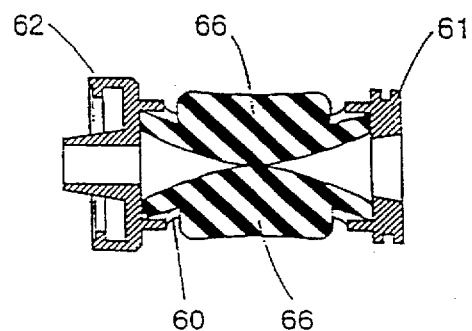
FIG. 9 shows the embodiment of FIG. 8 in cross section fully compressed.

FIGS. 7, 8 and 9 show views of alternative embodiments of cannula adaptors according to this invention which can be connected into existing cannulas by means of connectors 61 and 62 at each end of the body 60. The body includes a portion 64 which can be squeezed as in FIG. 7. FIG. 8 includes a portion 65 which has a button which can be pressed to close off the flow path. The cross section shown in FIG. 9 includes two buttons 66 which can be squeezed together to close off the flow path.

Figure 10:
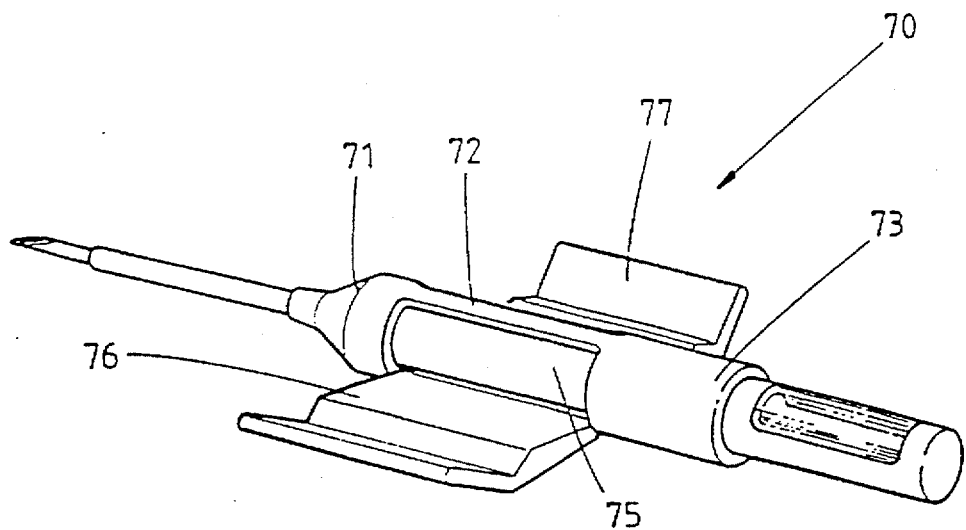
FIG. 10 shows a perspective view of an alternative embodiment of a catheter or cannula of the present invention.
Figure 11:
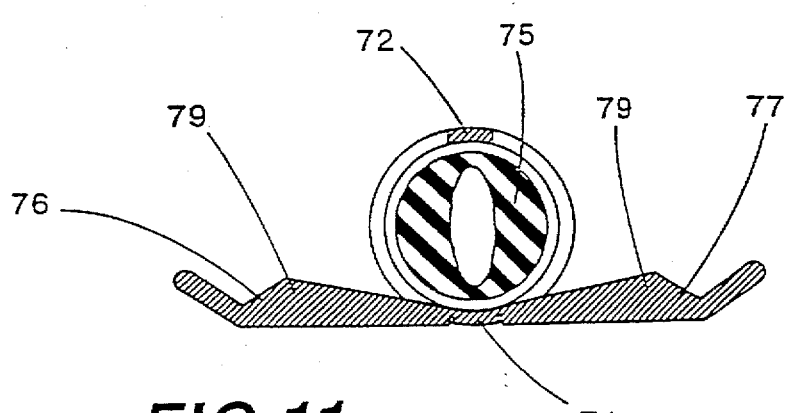
FIG. 11 shows a transverse cross sectional view of the cannula of FIG. 10, and FIG. 12, shows a transverse cross sectional view of the catheter or cannula of FIG. 10 with the pinch point compressed.
Figure 12:
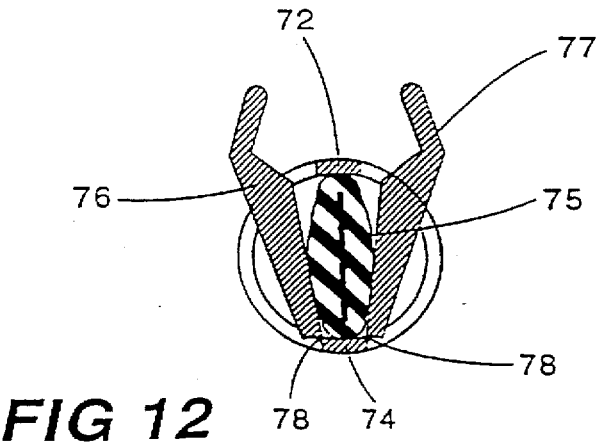

FIGS. 10, 11 and 12 show an alternative embodiment of a cannula according to this invention.

In this embodiment the cannula 70 includes a boss 71 and a frame assembly 72 and 74 connected to a connection portion 73. Between the boss 71 and the connection portion 73 is a flexible tube 75 which is adapted to be compressed to close off the flow path. The frame portion 74 includes wings 76 and 77 which are hinged to the frame portion 74 by means of integral hinges 78.

When it is desired to close off the flow path rather than squeezing the tube 75 directly the wings 76 and 77 may be hinged about the hinges 78 on the frame portion 74 so that the protuberances 79 on each wing actually compress the tube 75 to close it off.

By this means a more even pressure may be applied to the tube 75.

It will be realised that other embodiments of flexible tube as shown in the various embodiments of this invention may be used and rather than being of an elastic material the tube may include other means by which deformation may occur to close off the flow path. Such other means may include a helical or coiled spring which can be deformed to close off the flow path.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

I claim:

1. A cannula adapted to be mounted on to a trocar, the cannula incorporating a press point which is adapted to be resiliently deformed by externally applied pressure by at least one finger of a person during the insertion of the cannula and trocar assembly into a patient and removal of the trocar so as to prevent a flow of fluid through the cannula during the insertion and removal, and at least one integrally moulded hinged valve piece bearing against the press point and resiliently deform the press point to prevent flow through the cannula.

2. A cannula as in claim 1 wherein the press point includes one or more projections to thereby facilitate positive deformation of the press point.

3. A cannula as in claim 1 wherein the press point is comprised of flexible material.

4. A cannula as in claim 1 further comprising a body which comprises a first portion and a connector portion with the press point being between the first portion and the connector portion, wherein the first portion and the connector portion are connected by a frame arrangement and the press point is included on a flexible tube received into the frame arrangement between the first portion and the connector portion and sealingly engaging the first portion and the connector portion respectively.

5. A cannula as in claim 1 wherein the portion of the cannula which is adapted to be resiliently deformed is included on an adaptor piece which is adapted to be fitted to a cannula during insertion of the cannula and trocar assembly and removal of the trocar.

6. A cannula as in claim 5 wherein the adaptor piece comprises a first portion onto which the cannula tube is mounted and a connection portion which enables the adaptor piece to be connected to another item, wherein the press point is between the first portion and the connector portion, the first portion and the connector portion are connected by a frame arrangement, and the press point is included on a flexible tube received into the frame arrangement between the first portion and the connector portion and sealingly engaging the first portion and the connector portion respectively.

7. A cannula as in claim 6 wherein the flexible tube includes one or more projections to enable more positive deformation of the press point.

8. A cannula as in claim 6 wherein the one or more projections are buttons.

9. A cannula as in claim 1 further including a pair of valve pieces.

10. A cannula as in claim 9 wherein the valve pieces are spring loaded and biased to an open position.

11. A cannula as in claim 9 wherein the valve pieces are hinged on hinge axes aligned with the length of the cannula.

12. A cannula as in claim 1 further including wings extending from the cannula.

13. A cannula adapted to be mounted on to a trocar, the cannula incorporating a press point which is adapted to be resiliently deformed by externally applied pressure by at least one finger of a person during the insertion of the cannula and trocar assembly into a patient and removal of the trocar so as to prevent a flow of fluid through the cannula during the insertion and removal, wherein the cannula comprises a body and a cannula tube and the portion which is adapted to be resiliently deformed is part of the body and the press point includes at least one integrally moulded projection to thereby facilitate positive deformation of the press point, said at least one integrally moulded projection comprises valve pieces, said valve pieces being hinged to bear against the press point and resiliently deform the press point to thereby restrict flow through the cannula.

14. A cannula as in claim 13 wherein the press point comprises a flexible material.

15. A cannula as in claim 13 wherein the body comprises a first portion and a connector portion with the press point being between the first portion and the connector portion, wherein the first portion and the connector portion are connected by a frame arrangement and the press point is included on a flexible tube received into the frame arrangement between the first portion and the connector portion and sealingly engaging the first portion and the connector portion respectively.

16. A cannula as in claim 13 wherein the portion of the cannula which is adapted to be resiliently deformed is included on an adaptor piece which is adapted to be fitted to a cannula during insertion of the cannula and trocar assembly and removal of the trocar.

17. A cannula as in claim 16 wherein the adaptor piece comprises a first portion onto which the cannula tube is mounted and a connection portion which enables the adaptor piece to be connected to another item, wherein the press point is between the first portion and the connector portion, the first portion and the connector portion are connected by a frame arrangement, and the press point is included on a flexible tube received into the frame arrangement between the first portion and the connector portion and sealingly engaging the first portion and the connector portion respectively.

18. A cannula as in claim 13 wherein the valve pieces are spring loaded and biased to an open position.

19. A cannula as in claim 18 wherein the valve pieces are hinged on a hinged axis aligned with the length of the cannula.

20. A cannula as in claim 13 further including wings extending from the body.

21. A cannula as in claim 13 wherein the one or more projections are buttons.

22. A cannula including a body and a cannula tube, the body including a first portion into which the catheter tube is mounted and a connection portion which enables the cannula to be connected to another item, the cannula further including a press point associated with the body between the first portion and the connector portion, the press point being adapted to be pinched by externally applied pressure to restrict flow through the cannula during insertion of the cannula into a patient, wherein the first portion and the second portion are connected by a frame arrangement and the press point is included on a flexible tube received into the frame arrangement between the first portion and the connector portion and sealingly engaging the first portion and the second portions respectively and the press point includes at least one integrally moulded projection extending outwardly of the frame arrangement to thereby facilitate positive compression of the press point, said at least one integrally moulded projection comprises valve pieces, said valve pieces being hinged to bear against the press point and resiliently deform the press point to thereby restrict flow through the cannula.

23. A cannula as in claim 22 wherein the valve pieces are spring loaded and biased to an open position.

24. A cannula as in claim 22 wherein the valve pieces are hinged on hinge axes aligned with the length of the cannula.

25. A cannula as in claim 22 further including wings extending from the body.

26. A cannula as in claim 22 wherein the portion of the cannula which is adapted to be resiliently deformed is included on an adaptor piece which is adapted to be fitted to a cannula during insertion of the cannula.

27. A cannula as in claim 22 wherein the one or more projections are buttons.

28. An adaptor piece for a cannula, the adaptor piece comprising a first end portion into which the cannula tube may be mounted and a connection end portion to enable the adaptor piece to be connected to another item, the adaptor piece further including a press point between the first end portion and the connector end portion, wherein the first end portion and the second end portion are connected by a frame arrangement and the press point is included on a flexible tube received into the frame arrangement between the first end portion and the connector end portion and sealingly engaging the first end portion and the second end portion respectively and the flexible tube includes at least one integrally moulded projection to thereby facilitate positive deformation of the press point said at least one integrally moulded projection comprises valve pieces said valve pieces, being hinged to bear against the press point and resiliently deform the press point to thereby restrict flow through the cannula.

29. A cannula as in claim 28 wherein the one or more projections are buttons.

* * * * *